(12) United States Patent
Ochsner et al.

(10) Patent No.: US 11,045,640 B2
(45) Date of Patent: Jun. 29, 2021

(54) BIOMEDICAL APPARATUS WITH A PRESSURE-REGULATED BLOOD PUMP

(71) Applicant: ETH Zurich, Zurich (CH)

(72) Inventors: Gregor Ochsner, Einsiedeln (CH); Marianne Schmid Daners, Schaffhausen (CH); Raffael Amacher, Pfaeffikon (CH); Mirko Meboldt, Constance (DE); Volkmar Falk, Berlin (DE); Anastasios Petrou, Zurich (CH); Markus Wilhelm, Kilchberg (CH); Barbara Röhrnbauer, Zurich (CH)

(73) Assignee: ETH Zurich, Zurich (CH)

( * ) Notice: Subject to any disclaimer, the term of this patent is extended or adjusted under 35 U.S.C. 154(b) by 231 days.

(21) Appl. No.: 16/081,165

(22) PCT Filed: Mar. 2, 2017

(86) PCT No.: PCT/EP2017/054929
§ 371 (c)(1),
(2) Date: Aug. 30, 2018

(87) PCT Pub. No.: WO2017/149083
PCT Pub. Date: Sep. 8, 2017

(65) Prior Publication Data
US 2019/0076588 A1 Mar. 14, 2019

(30) Foreign Application Priority Data
Mar. 2, 2016 (EP) .................................... 16158181

(51) Int. Cl.
*A61M 60/50* (2021.01)
*A61M 60/148* (2021.01)
(Continued)

(52) U.S. Cl.
CPC .......... *A61M 60/148* (2021.01); *A61M 60/50* (2021.01); *A61M 60/405* (2021.01); *A61M 60/871* (2021.01)

(58) Field of Classification Search
CPC .. A61M 1/122; A61M 1/1068; A61M 1/1032; A61M 1/127
See application file for complete search history.

(56) References Cited

U.S. PATENT DOCUMENTS 6,540,699 B1 * 4/2003 Smith ...................... A61M 1/10
600/587
6,623,420 B2 9/2003 Reich et al.
(Continued)

FOREIGN PATENT DOCUMENTS

EP 2796156 A1 * 10/2014 ............... A61B 8/00
WO 03015609 A2 2/2003
(Continued)

*Primary Examiner* — Christopher Koharski
*Assistant Examiner* — James Moss
(74) *Attorney, Agent, or Firm* — The Webb Law Firm (57) ABSTRACT

A biomedical apparatus for pumping blood of a human or an animal patient through a secondary blood circuit is provided, including a blood pump, an inlet duct and an outlet duct for guiding blood of the patient to the blood pump and back to the patient. The apparatus further includes a measuring device with at least one pressure sensor for measuring pressure values in the patient's circulatory system. A controller is provided that includes at least two different preset control algorithms for regulating the operating point of the blood pump based on the measured pressure values. The controller is configured to select one of these preset control algorithms for being applied in dependence on the position of the at least one pressure sensor in the patient's circulatory system.

21 Claims, 2 Drawing Sheets

(51) Int. Cl.
    *A61M 60/405*     (2021.01)
    *A61M 60/871*     (2021.01)

(56) References Cited

U.S. PATENT DOCUMENTS

| | | |
|---|---|---|
| 7,476,200 B2 | 1/2009 | Tal |
| 2007/0073393 A1 | 3/2007 | Kung et al. |
| 2008/0097226 A1* | 4/2008 | McConnell .......... A61B 5/0215 600/485 |
| 2010/0222633 A1 | 9/2010 | Poirier |
| 2015/0306290 A1* | 10/2015 | Rosenberg ............ A61M 1/122 600/17 |

FOREIGN PATENT DOCUMENTS

| | | |
|---|---|---|
| WO | 2004073796 A2 | 9/2004 |
| WO | 2010099403 A1 | 9/2010 |

\* cited by examiner

BIOMEDICAL APPARATUS WITH A PRESSURE-REGULATED BLOOD PUMP

CROSS-REFERENCE TO RELATED APPLICATIONS

This application is the United States national phase of International Application No. PCT/EP2017/054929 filed Mar. 2, 2017, and claims priority to European Patent Application No. 16158181.4 filed Mar. 2, 2016, the disclosures of each of which are hereby incorporated by reference in their entireties.

BACKGROUND OF THE INVENTION

TECHNICAL FIELD

The present invention concerns a biomedical apparatus for pumping blood of a human or an animal patient through a secondary intra- or extracorporeal blood circuit, the biomedical apparatus comprising a blood pump which is regulated based on pressure-measurements carried out in in the patient's circulatory system. The invention also concerns a method for operating such a biomedical apparatus.

PRIOR ART

Various applications exist in which the blood of a human or an animal patient needs to be pumped through a secondary intra- or extracorporeal blood circuit. These applications include for example mechanical circulatory support by means of ventricular assist devices (VADs) or total artificial hearts, the circulation of blood by means of a heart-lung machine, also referred to as cardiopulmonary bypass, or extracorporeal membrane oxygenation (ECMO). These applications have in common that blood from a patient is guided to a blood pump by means of an inlet duct, and from the blood pump through an outlet duct back to the patient's circulatory system.

Ventricular assist devices (VADs) are used, when sufficient blood perfusion of patients with severe heart failure is to be restored by means of a mechanical blood pump. Even though the most preferred and accepted way to treat patients with severe heart failure is transplantation, VADs are often used to partly or completely restore the blood perfusion of the patients for bridging the time period until transplantation. While VADs have originally been developed for bridging to transplantation, the shortage of donor hearts has shifted the focus of clinicians and VAD developers to destination therapy and bridge to recovery. Bridge to recovery aims at later explantation of the VAD, due to recovery of the cardiac function during mechanical circulatory support. Destination therapy denotes the use of a VAD as a permanent implant. While recovery is the most desirable outcome of VAD therapy, only few patients show enough improvement in their cardiac function permitting the removal of the VAD. Thus, destination therapy remains a valid option for the treatment of severe heart failure.

VADs can be categorized into three pump-type generations. First generation VADs are pneumatically or electrically actuated pulsatile volumetric pumps. Pulsatile VADs imitate the working principle of the human heart and require a pump chamber and two unidirectional-flow valves. These devices are bulky and inefficient but provide a physiological perfusion. Pulsatile VADs are nowadays used mainly for bi-ventricular support, where the balance between the left and the right ventricle poses an additional problem. Second generation VADs are axial or centrifugal turbodynamic pumps with classical contact bearings. These devices exert a pressure on the blood by a spinning rotor in the blood stream. Modern, third generation VADs are axial or centrifugal turbodynamic pumps with a magnetically levitated rotor or with a blood-immersed bearing. Second and third generation devices are small, efficient, and more reliable. Compared to pulsatile VADs, these devices, however, provide non-physiological perfusion.

A problem with VADs and with biomedical apparatuses for pumping blood through a secondary intra- or extracorporeal blood circuit in general, concerns the controlling of the output power of the blood pump being used in these devices. Most clinically used turbodynamic VADs, for example, are operated at a constant speed and the perfusion of VAD patients therefore shows only a minor adaptation to the demand. The requirements for a physiological control of blood pumps, however, are manifold and potentially conflicting. Since a controller for a turbodynamic VAD, as an example, has only one degree of freedom—the pump speed—it is not possible to meet several requirements simultaneously. It is, however, possible to reduce the set of requirements to one task: The physiological controller must prevent overpumping or underpumping, and within these limits, adapt the pump speed to meet the patient's demand. Overpumping denotes a misactuation of the VAD where the pump speed is chosen too high, which can lead to a complete emptying of the ventricle and eventually to ventricular suction. Underpumping denotes the situation where the pump speed is chosen too low, which leads to backflow through the pump and a congestion of blood before the left ventricle. This congestion increases left atrial and pulmonary venous pressures and can eventually lead to lung edema. Stagnation or backflow in the pump additionally promotes hemolysis and thrombus formation, which is to be avoided.

In the document WO 2004/073796, methods are described for regulating the blood flow rate or blood pressure in a secondary blood circuit, in order to achieve a desired blood flow rate or blood pressure in the (primary) circulatory system of a patient. For regulating the blood pump, it is suggested in this document to monitor the blood flow rate or the blood pressure in the heart or in a blood vessel of the patient.

In US 2015/0306290 A1, a left ventricular assist device is disclosed that includes multiple independent sensors, in order to enable automatic speed control. It is proposed to also use a sensor that measures ventricular pressure.

Recently, VADs have been proposed in which the power regulation of a blood pump is inspired by the Frank-Starling law describing the physiological behaviour of the stroke volume of the heart depending on preload recruitable stroke work (Glower D D, Spratt J A, Snow N D, et al. Linearity of the Frank-Starling relationship in the intact heart: the concept of preload recruitable stroke work. Circ 1985; 71:994-1009). In these devices, the respective blood pumps are regulated in a physiological way, in order to improve the outcome of the VAD therapy.

US 2007/0073393 A1 discloses a blood pump the power of which is regulated based on measurements made by pressure sensors, wherein reference is made to the Frank-Starling law.

US 2008/0097226 A1 discloses a controller for regulating a blood pump according to the Frank-Starling law, wherein the controller varies the speed of the blood pump as a function of a combination of the heart rate and the left ventricular pressure. It is also disclosed in this document that left ventricular pressure values can be provided to the controller via wireless transmission.

Many devices that imitate the Frank-Starling law for the power regulation of a blood pump, however, still have problems with respect to robustness and reliability of the regulation mechanism. In particular, there are still major challenges to be solved that concern the pathological heart. In pathological hearts, the regulation mechanism is often unable to meet the perfusion requirements due to the weakness of the left ventricular wall.

SUMMARY OF THE INVENTION

Thus, it is an object of the present invention to provide a biomedical apparatus for pumping blood of a human or an animal patient through a secondary intra- or extracorporeal blood circuit, having a blood pump that is operated in a physiological, robust and reliable way. It is also an object of the present invention to provide a corresponding biomedical apparatus that can flexibly be applied in accordance to the needs and the limitations indicated by the respective patient.

In order to achieve this object, the present invention provides a biomedical apparatus for pumping blood of a human or an animal patient through a secondary intra- or extracorporeal blood circuit, comprising
  a blood pump for pumping blood,
  an inlet duct connected to the blood pump, for being inserted into a patient's circulatory system, in order to guide blood of the patient to the blood pump,
  an outlet duct connected to the blood pump, for being inserted into the patient's circulatory system, in order to guide blood from the blood pump back to the patient's circulatory system,
  at least one measuring device with at least one pressure sensor for measuring pressure values in the patient's circulatory system, and
  a controller for regulating the operating point of the blood pump based on the measured pressure values, wherein the controller comprises at least two different preset control algorithms for regulating the operating point of the blood pump based on the measured pressure values and is configured to select one of these preset control algorithms for being applied in dependence on the position of the at least one pressure sensor in the patient's circulatory system.

The operating point of the blood pump usually refers to the speed of the blood pump, i.e. in the case of a turbodynamic pump to the rotational speed of the rotor. Thus, the operating point can be regarded as an indicator of the blood flowing through the blood pump.

By comprising more than a single preset control algorithm for regulating the operating point the controller can be adapted to the needs and the limitations of the patient in a flexible and easy way. Such a biomedical apparatus having a controller with several different preset control algorithms for regulating the operating point of the blood pump can be configured for an almost arbitrary positioning of the pressure sensor(s) in the patient's circulatory system. In dependence on the position of the pressure sensor, the preset control algorithm can be selected which achieves an optimal operation of the blood pump based on the measured pressure values. Due to many reasons and in particular in pathological hearts, e.g. a preferred positioning of the pressure sensor in the left ventricle can be unfavourable for a patient. In such a case, the pressure sensor can for example be positioned in the pulmonary artery. In order to also achieve a reliable and robust operation of the blood pump in this case, a different and better suited control algorithm can be applied by the controller as compared to the situation in which the pressure sensor is positioned in the left ventricle. Thus, an optimal regulation of the blood pump can be achieved in each case.

A further advantage of having at least two different preset control algorithms for regulating the operating point of the blood pump is, that a pressure sensor can easily be exchanged in case of failure, in particular in the cases where the sensor is not embedded in the pump or the pump's inlet or outlet duct. Only the sensor needs to be replaced for this purpose. The blood pump and the controller do not necessarily have to be exchanged. If the controller is adapted to automatically detect the presence and the location of the pressure sensor(s), a particularly easy replacement and/or addition of pressure sensor(s) to the biomedical apparatus can be achieved.

The selection of the preset control algorithm of the controller can be done manually by the surgeon or the physician or by trained medical personnel, when implanting the biomedical apparatus or shortly thereafter.

In a preferred embodiment, however, the at least one measuring device is adapted to transmit an identifier to the controller, the identifier reflecting the position of the at least one pressure sensor in the patient's circulatory system. The identifier, for example in the form of a specific number, can be stored in a storage module of the measuring device. Preferably, the controller is configured to select one of the preset control algorithms for being applied in dependence on the identifier transmitted by the at least one measuring device. For this purpose, an assignment table can be stored in a storage module of the controller, in which assignment table one of the preset control algorithms is assigned to each of the identifiers. Thus, in such an embodiment, the controller is preferably adapted to automatically select one of the preset control algorithms based on the received identifier and to apply the respective preset control algorithm to regulate the operating point of the blood pump.

In a preferred embodiment, the at least two different preset control algorithms of the controller are at least two of the following four control algorithms:
  a first control algorithm, according to which an estimate for the preload of the heart is determined based on an identification of a maximum of the measured pressure values, in order to regulate the operating point of the blood pump based on this determined estimate for the preload of the heart,
  a second control algorithm, according to which an estimate for the preload of the heart is determined based on an identification of a minimum of the measured pressure values, in order to regulate the operating point of the blood pump based on this determined estimate for the preload of the heart,
  a third control algorithm, according to which a temporal mean value of the measured pressure values over at least one cardiac cycle is calculated, in order to regulate the operating point of the blood pump based on this calculated temporal mean value, and
  a fourth control algorithm, according to which a pressure at a specific point in time during the cardiac cycle is identified based on the measured pressure values, in order to regulate the operating point of the blood pump based on this identified pressure.

Thus, in this preferred embodiment, the controller comprises at least two control algorithms of the group of this first, this second, this third, and this fourth control algorithm. The controller can also comprise three preset control algorithms of this group of four control algorithms. It is also possible for the controller to comprise all of these four preset control algorithms.

Preferably, the controller is configured to apply one of the preset control algorithms in every cardiac cycle. Thus, the feature extraction according to the applied control algorithm is preferably repeated in every cardiac cycle, in order to correspondingly re-adjust the operating point of the blood pump after every heartbeat.

The controller preferably comprises the first or the fourth control algorithm as one of the at least two preset control algorithms, if at least one pressure sensor is configured to measure the pressure values inside of the left ventricle or the right ventricle of the heart of the patient. Accordingly, the controller is advantageously configured to select the first or the fourth control algorithm for being applied to regulate the operating point of the blood pump, if the at least one pressure sensor is positioned to measure the pressure inside of the left ventricle or the right ventricle of the heart of the patient.

The estimate for the preload of the heart can be determined in a particularly easy way by this first control algorithm, if a maximum pressure value of the measured pressure values over each time interval of e.g. at least one cardiac cycle is identified as the estimate for the preload of the heart. By applying the first control algorithm, a particularly reliable and robust operation of the blood pump can be achieved, if the at least one pressure sensor is positioned inside of the left ventricle or the right ventricle. The controller is preferably configured to identify the maximum of the measured pressure values over a cardiac cycle, advantageously over each cardiac cycle.

The use of the fourth control algorithm leads to a particularly precise estimate for the preload of the heart. The controller can in this case for example be configured to detect the time where end-diastole occurs as the specific point in time for identifying the pressure to regulate the operating point of the blood pump. The specific point in time during the cardiac cycle as used by this fourth control algorithm can for example be determined based on an ECG measurement or based on the measured pressure values.

The controller preferably comprises the second control algorithm as one of the at least two preset control algorithms, if at least one pressure sensor is configured to measure the pressure values inside of the pulmonary arterial circulation of the patient. Accordingly, in this case the controller is advantageously configured to select the second control algorithm for being applied to regulate the operating point of the blood pump, if the at least one pressure sensor is positioned inside of the pulmonary arterial circulation of the patient. The estimate for the preload of the heart can be determined in a particularly easy way by this second control algorithm, if a minimum pressure value of the measured pressure values over each time interval of e.g. at least one cardiac cycle is identified as the estimate for the preload of the heart. By applying the second control algorithm, a particularly reliable and robust operation of the blood pump can be achieved, if the at least one pressure sensor is positioned inside of the pulmonary arterial circulation. The controller is preferably configured to identify the minimum of the measured pressure values over a cardiac cycle, advantageously over each cardiac cycle.

The controller preferably comprises the third control algorithm as one of the at least two preset control algorithms, if at least one pressure sensor is configured to measure the pressure values inside of the left atrium or the right atrium of the heart or inside of the pulmonary or systemic vein of the patient. Accordingly, in this case the controller is advantageously configured to select the third control algorithm for being applied to regulate the operating point of the blood pump, if the at least one pressure sensor is positioned inside of the left atrium or the right atrium of the heart or inside of the pulmonary or systemic vein of the patient. By applying the third control algorithm, a particularly reliable and robust operation of the blood pump can be achieved, if the at least one pressure sensor is positioned inside of the left atrium or the right atrium or inside of the pulmonary or systemic vein.

Each of the first, second, third and fourth control algorithm for operating the blood pump is inspired by the Frank-Starling law describing the physiological behaviour of the heart. According to this law, the stroke volume of the heart increases in response to an increase in the preload of the heart when all other factors remain constant. With the first and second control algorithms, an estimate for the preload of the heart is determined for regulating the blood pump. The temporal mean value calculated in the third control algorithm and the pressure at a specific point in time during the cardiac cycle as identified in the fourth control algorithm can, in most embodiments, also be regarded as an estimate for the preload of the heart. While the left ventricular end-diastolic pressure represents a direct indicator of the cardiac preload, it has been recognized in the context of the present invention that also the minimum pressure over the cardiac cycle and the left ventricular peak-systolic pressure and the temporal mean value of certain pressure values and the minimum (diastolic) pulmonary arterial pressure can be used as good estimates for the preload of the heart, especially in situations in which the end-diastolic pressure is not detectable in a sufficiently robust and reliable way. Thus, by determining an estimate for the preload of the heart and by using this estimate for regulating the operating point of the blood pump, a very physiological way of regulating the blood pump is provided, in which the controller adapts the pump speed according to the patient's perfusion demand. Hence, the controller is able to adapt the cardiac output very similarly to the physiological heart. By using an estimate for the cardiac preload, in order to control the blood pump, over- and underpumping are usually effectively prevented without any further measures.

The duration of the time interval for identifying the maximum or minimum pressure values in the first and second control algorithm, respectively, or for calculating the temporal mean value in the third control algorithm is preferably more than 1.3 seconds, more preferably from 1.5 to 2.5 seconds, and most preferably about 2 seconds.

In order to achieve an optimal physiological regulation of the blood pump, the biomedical apparatus is preferably configured to measure the pressure values with a temporal resolution of less than 400 ms, more preferably of less than 200 ms, and most preferably of less than 100 ms. The controller can be configured to adapt the operating point of the blood pump with the same temporal resolution. The temporal resolution for adapting the operating point of the blood pump can, however, also be more than a cardiac cycle, such as for example 1.5 to 2.5 seconds.

In the following, further possible control algorithms for regulating the operating point of the blood pump are described which can be preset in the controller.

In a further preset control algorithm, an estimate for the blood flow through the blood pump can be determined. For this purpose, the pressure as detected by a pressure sensor positioned on or in the inlet duct can be used, preferably in combination with the values of the electrical current applied for driving the blood pump and/or of the speed of the blood pump.

In another further preset control algorithm, an estimate for the minimum flow through the blood pump can be determined for each heartbeat or averaged over several heartbeats. Based on this determined estimate for the minimum flow through the blood pump, the controller can for example increase the speed of the blood pump in case a backflow is detected.

In another further preset control algorithm, an estimate for the end-diastolic pressure can be determined, in order to increase the speed of the blood pump, if the determined estimate for the end-diastolic pressure is above a predefined value (e.g. 20 mmHg). In doing so, an overload of the left and/or the right ventricle can be prevented. The estimation for the end-diastolic pressure can be based on a pressure sensor positioned on or in the inlet duct. Alternatively, any other estimate that represents the loading of the circulation could be determined in such a further preset control algorithm for preventing an overload of the left and/or the right ventricle, particularly in the case of a pressure sensor being positioned in the pulmonary artery.

In another further preset control algorithm, an estimate for the maximum of the measured pressure values can be determined for each heartbeat as well as an estimate for the blood flow through the blood pump. Based on these estimates, the pump speed can be decreased, in case a possible negative pressure is detected.

In another further preset control algorithm, an estimate for the moment of aortic valve opening can be determined, e.g. for each heartbeat. For this purpose, the values of the electrical current applied for driving the blood pump and/or of the speed of the blood pump can for example be used, possibly in combination with an estimate for the blood flow through the blood pump. The blood pump can then be controlled in such a way by the controller that the opening and closing of the aortic valve occurs at certain predefined time points.

In another further preset control algorithm, an estimate for the contractility of the left and/or the ventricle can be determined. For this purpose, estimates for the blood flow through the blood pump, for the end-diastolic pressure and/or for the maximum gradient of the pressure at the inlet duct can for example be used. Thus, possible changes of the contractility of the ventricle can be identified, in order to accordingly adapt the regulation of the blood pump.

In another further preset control algorithm, an estimate for the flow through the blood pump and/or for the pressure at the inlet duct can be used to identify changes of stiffness and/or relaxation properties of the left or the right ventricle. Thus, possible changes of the stiffness of the ventricle can be identified, in order to accordingly adapt the regulation of the blood pump.

In another further preset control algorithm, an estimate for the mean aortic pressure can be determined, in order to monitor the afterload of the heart. For this purpose, estimates for the moment of aortic valve opening, for the diastolic aortic pressure as detected or estimated by the maximum gradient of the pressure at the inlet duct and/or for the systolic aortic pressure as detected or estimated by the maximum of the pressure at the inlet duct are preferably determined and used. In doing so, the assumption can be made that the diastolic aortic pressure equals the inlet duct pressure at the time where the maximum of the gradient of the inlet duct pressure occurs.

In another further preset control algorithm, an estimate for the heart rate can be determined based on a detection of the maxima of the measured pressure values, in order to estimate the heart rate variability.

In another further preset control algorithm, an estimate for the blood viscosity can be determined as an indicator for haematocrit of the patient. For this purpose, an estimate for the blood flow through the blood pump in combination with the values of the electrical current applied for driving the blood pump and/or of the speed of the blood pump as well as optionally an estimate for the flow through the blood pump can be used.

In another further preset control algorithm, an estimate for the blood flow through the aortic valve can be determined. For this purpose, an estimate for the mean aortic pressure, in particular for the outlet pressure of the aortic valve, is preferably used together with an estimate for the inlet valve pressure as an input for a valve model. The inlet valve pressure is preferably assumed to be equal as the pressure measured at or in the inlet duct.

The preset control algorithms as set out above can of course also be present in combined forms, in order to control the blood pump by means of the controller.

The first, second, third and fourth preset control algorithms as well as the further possible control algorithms as described above can of course also be applied in biomedical apparatuses which for example do not allow an arbitrary positioning of the pressure sensor in the patient's circulatory system and/or which provide this control algorithm as a single preset control algorithm for regulating the operating point of the blood pump.

Therefore, the present invention also provides the biomedical apparatuses as follows:

A biomedical apparatus for pumping blood of a human or an animal patient through a secondary intra- or extracorporeal blood circuit, in particular a biomedical apparatus as indicated above, comprising a blood pump for pumping blood,
an inlet duct connected to the blood pump, for being inserted into a patient's circulatory system, in order to guide blood of the patient to the blood pump,
an outlet duct connected to the blood pump, for being inserted into the patient's circulatory system, in order to guide blood from the blood pump back to the patient's circulatory system,
at least one measuring device with at least one pressure sensor for measuring pressure values in the patient's circulatory system, and
a controller for regulating the operating point of the blood pump based on the measured pressure values, wherein the controller comprises at least one preset control algorithm for regulating the operating point of the blood pump, according to which control algorithm an estimate for the preload of the heart is determined based on an identification of a maximum of the measured pressure values, in order to regulate the operating point of the blood pump based on this determined estimate for the preload of the heart.

A biomedical apparatus for pumping blood of a human or an animal patient through a secondary intra- or extracorporeal blood circuit, in particular one of the biomedical apparatuses as indicated above, comprising a blood pump for pumping blood,
an inlet duct connected to the blood pump, for being inserted into a patient's circulatory system, in order to guide blood of the patient to the blood pump, an outlet duct connected to the blood pump, for being inserted into the patient's circulatory system, in order to guide blood from the blood pump back to the patient's circulatory system, at least one measuring device with at least one pressure sensor for measuring pressure values in the patient's circulatory system, and a controller for regulating the operating point of the blood pump based on the measured pressure values, wherein the controller comprises at least one preset control algorithm for regulating the operating point of the blood pump, according to which control algorithm an estimate for the preload of the heart is determined based on an identification of a minimum of the measured pressure values, in order to regulate the operating point of the blood pump based on this determined estimate for the preload of the heart.

A biomedical apparatus for pumping blood of a human or an animal patient through a secondary intra- or extracorporeal blood circuit, in particular one of the biomedical apparatuses as indicated above, comprising a blood pump for pumping blood, an inlet duct connected to the blood pump, for being inserted into a patient's circulatory system, in order to guide blood of the patient to the blood pump, an outlet duct connected to the blood pump, for being inserted into the patient's circulatory system, in order to guide blood from the blood pump back to the patient's circulatory system, at least one measuring device with at least one pressure sensor for measuring pressure values in the patient's circulatory system, and a controller for regulating the operating point of the blood pump based on the measured pressure values, wherein the controller comprises at least one preset control algorithm for regulating the operating point of the blood pump, according to which control algorithm a temporal mean value is calculated of the measured pressure values over at least one cardiac cycle, in order to regulate the operating point of the blood pump based on this calculated temporal mean value.

A biomedical apparatus for pumping blood of a human or an animal patient through a secondary intra- or extracorporeal blood circuit, in particular one of the biomedical apparatuses as indicated above, comprising a blood pump for pumping blood, an inlet duct connected to the blood pump, for being inserted into a patient's circulatory system, in order to guide blood of the patient to the blood pump, an outlet duct connected to the blood pump, for being inserted into the patient's circulatory system, in order to guide blood from the blood pump back to the patient's circulatory system, at least one measuring device with at least one pressure sensor for measuring pressure values in the patient's circulatory system, and a controller for regulating the operating point of the blood pump based on the measured pressure values, wherein the controller comprises at least one preset control algorithm for regulating the operating point of the blood pump, according to which control algorithm a pressure at a specific point in time during the cardiac cycle is identified based on the measured pressure values, in order to regulate the operating point of the blood pump based on this identified pressure value.

Each of the biomedical apparatuses as indicated is preferably a Mechanical Circulatory Support (MCS) device, more preferably a Ventricular Assist Device (VAD) and most preferably a Left Ventricular Assist Device (LVAD). The biomedical apparatus can, however, also be a total artificial heart, a heart-lung machine or an extracorporeal membrane oxygenation (ECMO) apparatus. Further types of biomedical apparatuses are conceivable, such as for example a dialysis apparatus. Depending on the type of apparatus, the blood is pumped through a secondary intra- or extracorporeal blood circuit. The secondary blood circuit here refers to an additional, artificial circuit, in which blood from the (primary) circulatory system of the patient is guided to the blood pump, which pumps the blood back into the circulatory system of the patient. Within the secondary blood circuit, the blood can optionally be treated in a certain way. For example, the blood can be oxygenated (ECMO, cardiopulmonary bypass), or waste and excess water can be removed from the blood (dialysis). In these cases, in which a treatment of the blood is carried out, the secondary blood circuit is usually an extracorporeal blood circuit. In cases, in which the main function of the biomedical apparatus is to support or to replace at least a part of the function of the heart, such as in the case of a VAD, the secondary blood circuit is preferably, but not necessarily, an intracorporeal blood circuit, i.e. a blood circuit being entirely arranged within the body of the patient.

The inlet duct and the outlet duct of the biomedical apparatuses usually have a tubular form. They can be represented for example by flexible tubes. Preferably, however, the inlet duct is an inlet cannula and/or the outlet duct is an outlet cannula. Especially if the biomedical apparatus is a VAD, the inlet duct is advantageously adapted for being inserted into the heart, more advantageously for being inserted into one of the ventricles, and most advantageously for being inserted into the left ventricle, of the patient. In the case of a VAD, the outlet duct is preferably adapted to be connected with the aorta of the patient. It is possible for at least one pressure sensor to be arranged on the inlet duct or the outlet duct.

The biomedical apparatus usually comprises a housing in which the blood pump and preferably also the controller are located. The apparatus usually also comprises an energy storage device, such as a battery or accumulator, or an electrical power connector for connecting the apparatus to an electrical power supply, in order to supply the blood pump with energy. The energy storage device is advantageously included in the housing of the apparatus. Further energy storage devices, such as batteries or accumulators, or electrical power connectors can also be provided for each of the measuring devices.

The blood pump is preferably a pneumatically or electrically actuated pump. Other types of pumps, such as hydraulically actuated pumps, are also conceivable of course. The blood pump can be a pulsatile volume displacement pump or a pump relying on a rotating impeller. The pump can particularly be a turbodynamic pump, such as an axial or a centrifugal turbodynamic pump, which can comprise classical contact bearings, a magnetically levitated rotor or a blood-immersed bearing. The invention can also be used with other, less commonly applied types of blood pumps.

In certain embodiments, the at least one measuring device can comprise a send-unit and the controller can comprise a receive-unit, in order to wirelessly transmit a signal that reflects the measured pressure values from the at least one measuring device to the controller. No cable connections between the measuring device and the controller need to be provided in such a case. It is particularly advantageous in such an embodiment, if the measuring device is adapted to transmit an identifier to the controller for indicating the position of the at least one pressure sensor to the controller.

The send-unit of the measuring device does not necessarily be an active send-unit, but can also be provided by a passive data transmission circuit. In this case, the apparatus, preferably the controller, would comprise a read-out circuit, which is able to excite the passive data transmission circuit of the at least one measuring device such that a e.g. frequency-modulated signal reflecting the measured pressure values is received.

Optionally, but not necessarily, the biomedical apparatus can comprise a suction detector, in order to prevent ventricular or vascular suction. The suction detector can be used as an add-on to the physiological regulation of the blood pump based on the measured physical parameter. As soon as suction occurs, the suction detector detects it and a suction release strategy can be initiated, which temporarily overrules the selected control algorithm.

Preferably, the controller is configured to regulate the operating point of the blood pump such that a linear relationship is established between the estimate for the preload of the heart or the temporal mean value or the pressure at a specific point in time during the cardiac cycle on the one hand and the power, e.g. the hydraulic power, of the blood pump on the other hand. A linear relation between the estimate for the cardiac preload and the resulting left ventricular stroke volume corresponds to the Frank-Starling law and, thus, results in not only a simple, but also a physiological regulation of the blood pump.

The biomedical apparatus can further comprise a high-pass filter for filtering a signal that reflects the measured pressure values. The high-pass filter is preferably designed such that a possible long-term drift of the at least one pressure sensor is eliminated from the signal, but that day/night cycles are still reflected in the signal. The high-pass filter can be a second-order infinite impulse response (IIR) filter. The cut-off frequency of the filter is preferably chosen between approximately $1/(1\ \text{day})=1.15*10^{-5}$ Hz and $1/(2\ \text{days})=5.79*10^{-6}$ Hz, more preferably at approximately $1*10^{-5}$ Hz.

The controller can comprise at least one preset special control algorithm for regulating the power, in particular the hydraulic power, of the blood pump. In such a case, the controller is preferably configured to select this special control algorithm for being applied, if a signal that reflects the measured pressure values exceeds a certain upper and/or lower limit, or if the desired power, in particular hydraulic power, of the blood pump exceeds certain upper and/or lower limits. By providing the special control algorithm it is ensured that the regulation of the blood pump is kept within certain limits.

The controller can be configured to detect malfunctions of the at least one pressure sensor automatically and further be configured to switch automatically to another control algorithm using another pressure sensor, or disable the control algorithm, in case of a detected malfunction. Thus, the controller can comprise a safety algorithm which will disable any control algorithm that is based on the measured pressure signal originating from a malfunctioning pressure sensor. Instead, this safety algorithm will return the pump to a safe operating mode, in which for example a manually defined operating point is used.

In order to achieve a physiological operation of the blood pump, the controller can be adapted to superimpose the regulation of the operating point of the blood pump with a periodic signal being synchronized to the cardiac cycle. The periodic signal can for example be sinusoidal or have square waves. This periodic signal may have the same frequency as the heart rate, and it can be synchronized to the cardiac cycle using the measured blood pressure, for example by extracting a specific index of the measured blood pressure, e.g. a maximum of the measures pressure values, or it can be synchronized to the cardiac cycle using another measurement, for example an additional electrocardiogram (ECG) measurement, or the periodic signal can even be asynchronous to the heart rate or have a variable frequency. The purpose of superimposing such a periodic signal is to enhance certain hemodynamic parameters, such as the arterial pulsatility, the flow through the aortic valve, or the stroke work of the left ventricle. If such a signal is present, it is preferably designed such that it does not interfere with the capability of the controller of imitating the Frank-Starling law of the heart. The periodic signal can be stored in the controller and/or be predefined in shape, e.g. a sine wave. It can be parameterized and certain parameters can be changed online either manually or automatically, e.g. by means of the measured pressure values or by measuring or estimating the pump flow based on the electrical current, the speed and/or the pressure of the blood pump. For example, the amplitude of the periodic signal can be controlled such as to prevent backflow.

The current invention also relates to a method for operating a biomedical apparatus for pumping blood of a human or an animal patient through a secondary intra- or extracorporeal blood circuit, in particular one of the biomedical apparatuses as indicated, wherein the biomedical apparatus comprises a blood pump for pumping blood, an inlet duct connected to the blood pump, for being inserted into a patient's circulatory system, in order to guide blood of the patient to the blood pump, an outlet duct connected to the blood pump, for being inserted into the patient's circulatory system, in order to guide blood from the blood pump back to the patient's circulatory system, and at least one measuring device with at least one pressure sensor, and wherein the method comprises at least the following steps:

measuring pressure values in the patient's circulatory system by means of the at least one pressure sensor, and regulating the operating point of the blood pump based on the measured pressure values.

In this method, the position of the at least one pressure sensor in the patient's circulatory system is determined and one of at least two different preset control algorithms for regulating the operating point of the blood pump is then selected based on the measured pressure values for being applied in dependence on the determined position of the at least one pressure sensor in the patient's circulatory system.

BRIEF DESCRIPTION OF THE DRAWINGS

Preferred embodiments of the invention are described in the following with reference to the drawings, which only serve for illustration purposes, but have no limiting effects. In the drawings it is shown.

DESCRIPTION OF THE INVENTION

Figure 1:
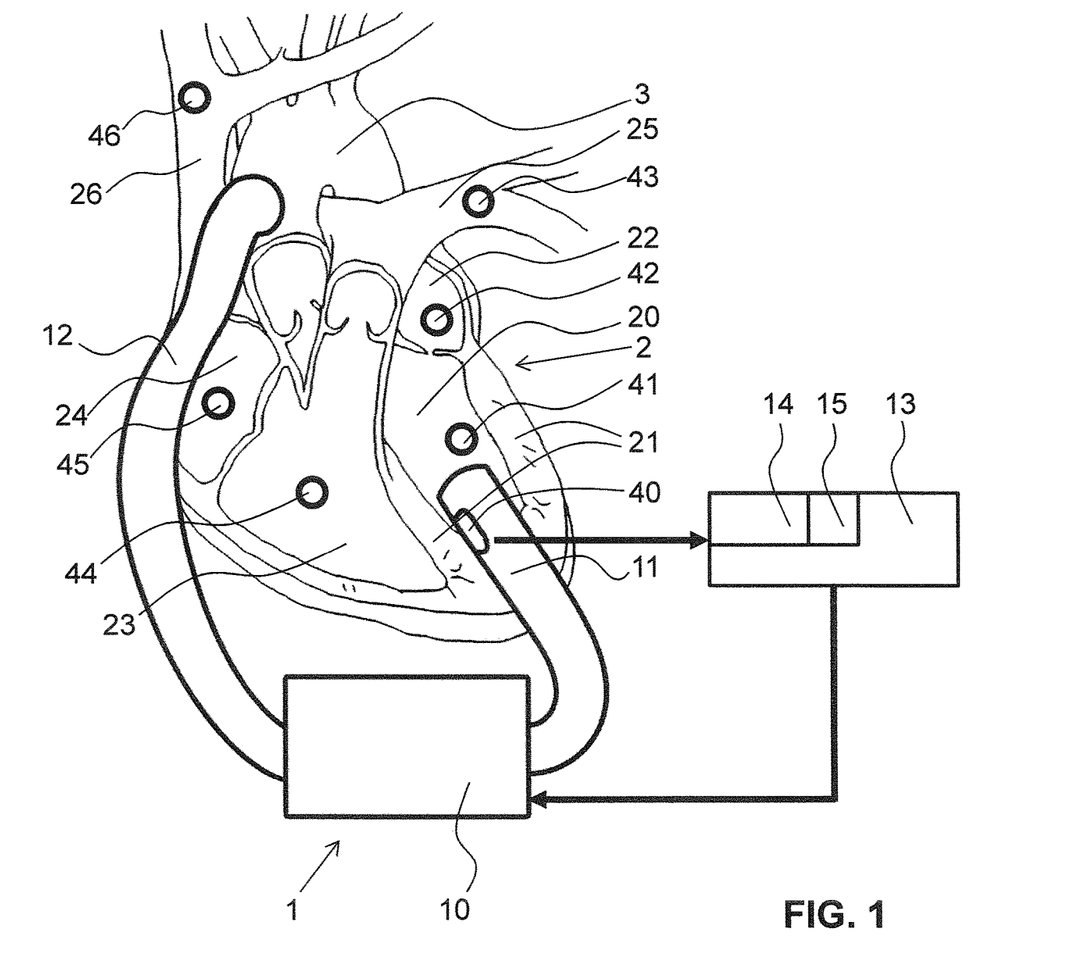
FIG. 1 a schematic view of a Ventricular Assist Device (VAD) according to the invention, implanted in the heart of a patient.

In FIG. 1, an inventive embodiment of a biomedical apparatus for pumping blood of a human or an animal patient through a secondary intra- or extracorporeal blood circuit is shown. The apparatus of this embodiment is a Mechanical Circulatory Support (MCS) device in the form of a Left Ventricular Assist Device (LVAD) 1 used to partially or completely replace the function of a heart 2 of a patient with heart failure.

The VAD 1 comprises a blood pump 10, which can be a pneumatically or electrically actuated pulsatile volumetric pump or, which is preferred, an axial or centrifugal turbodynamic pump with classical contact bearings, with a magnetically levitated rotor or with a blood-immersed bearing, or other less commonly applied types of pumps. A large variety of pumps of these kinds and suited for being used as a VAD are known to the person skilled in the art.

Connected to the blood pump 10 is an inlet duct or, here, an inlet cannula 11, which has a free end being inserted into the left ventricle 20 in the region of the apex of the heart 2. The inlet cannula 11 serves to guide blood from the inside of the left ventricle 20 to the blood pump 10. Due to the pumping action of the blood pump 10 the blood is drawn through an inlet opening located at the free end of the inlet cannula 11 into the inlet cannula 11 and to the blood pump 10.

In direction of the blood stream, an outlet duct or, here, an outlet cannula 12 is connected to the blood pump 10 on the opposite side relative to the inlet cannula 11. The outlet cannula 12 serves to guide the blood from the blood pump 10 back to the patient's circulatory system. To this end, the outlet cannula 12 is inserted into the aorta 3 of the patient.

The inlet cannula 11, the blood pump 10 and the outlet cannula 12 together constitute a secondary blood circuit, which is preferably located completely inside the body of the patient. The blood streaming through this secondary blood circuit originates from the left ventricle 20 and streams into the aorta 3. Within the secondary blood circuit, the blood is pumped by the blood pump 10 in the direction towards the aorta 3. Thus, the blood pump 10 supports the function of the (failed) heart 2.

The output power by which the blood is pumped into the outlet cannula 12 by the blood pump 10 is regulated by a controller 13 which is able to communicate with a measuring device 4 comprising a pressure sensor 40 attached to the inlet cannula 11. The connections of the controller 13 to the pressure sensor 40 on the one hand and to the blood pump 10 on the other hand are indicated in FIG. 1 by means or respective arrows.

In FIG. 1, only the pressure sensor 40 and the alternative or additional pressure sensors 41-46, as described below, of the measuring devices 4 are shown. The measuring device 4 is shown schematically in detail in FIG. 2.

Alternatively to the measuring device with the pressure sensor 40, the biomedical apparatus can comprise a measuring device 4 with a pressure sensor 41, 42, 43, 44, 45 or 46 that is not positioned at the inlet cannula 11, but at a remote position with respect to the blood pump 10, the controller 13 and the inlet and outlet ducts 11 and 12.

For example, an alternative measuring device 4 can comprise a pressure sensor 41 that is positioned inside of the left ventricle 20, but remote from the inlet cannula 11. The measuring device 4 comprising such a pressure sensor 41 can be attached to the inner surface of the ventricular wall 21 or can even extend through the ventricular wall 21.

An alternative measuring device 4 can also comprise a pressure sensor 42 that is positioned in the left atrium 22. It is also possible to provide a measuring device 4 having a pressure sensor 43 which is positioned in the pulmonary artery 25 or having a pressure sensor 44 in the right ventricle 23. Furthermore, it is possible to arrange a pressure sensor 45 in the right atrium 24. An arrangement of a pressure sensor 46 in the systemic vein 26 is also conceivable.

Each of the measuring devices 4 with pressure sensors 41-46 can be positioned completely inside of the respective ventricle 20 or 23, atrium 22 or 24, artery 25 or vein 26 and be attached, for example, to an inner wall of the heart 2 or of the respective blood vessel. It is, however, also possible that the measuring device 4 with one of the sensor 41-46 extends through a wall of the heart 2 or of a blood vessel in such a way that the sensor is still able to measure pressure values inside of the heart 2 or blood vessel.

The measuring devices 4 and in particular the pressure sensors 40-46 are preferably designed such that they are specifically adapted and optimized for being positioned at a particular place in the circulatory system of the patient. It is of course also conceivable to provide alternative measuring devices 4 with corresponding pressure sensors that are positioned at other places of the circulatory system than shown in FIG. 1. Such other places can particularly be arranged more distant from the heart 2 than the ones shown in FIG. 1.

It is also possible to have more than a single pressure sensor per measuring device 4, and it is even possible to have more than a single measuring device 4 with each measuring device 4 comprising one or more pressure sensors.

Each of the measuring devices 4 with one of the pressures sensors 40-46 is connected to the controller 13 in such a way that measured pressure values can be transmitted from the measuring device 4 to the controller 13. An arrow representing a respective connection is only shown for pressure sensor 40 in FIG. 1, but of course corresponding connections between the pressure sensor and the controller 13 are also present for pressure sensors 41-46.

The connections between the pressure sensors 40-46 and the controller 13 for transmitting a signal that reflects the measured pressure values can be achieved by providing respective cable and/or wireless connections. In the case of cable connections, the measured pressure values can be transmitted electrically or optically by means of corresponding electric or optical cables connecting each of the measuring devices 4 with the controller 13.

In the case of wireless connections, each of the respective measuring devices 4 comprises a send-unit that is adapted to wirelessly transmit a signal reflecting the measured pressure values. The controller 13 then comprises a corresponding receive-unit which is able to receive the signals transmitted by the send-units of the measuring devices 4. In order to enable a two-way communication, it is preferred to provide the measuring devices 4 and the controller 13 with a send/receive-unit 47 and 14, respectively, that is able to both send and receive wireless data signals.

Figure 2:
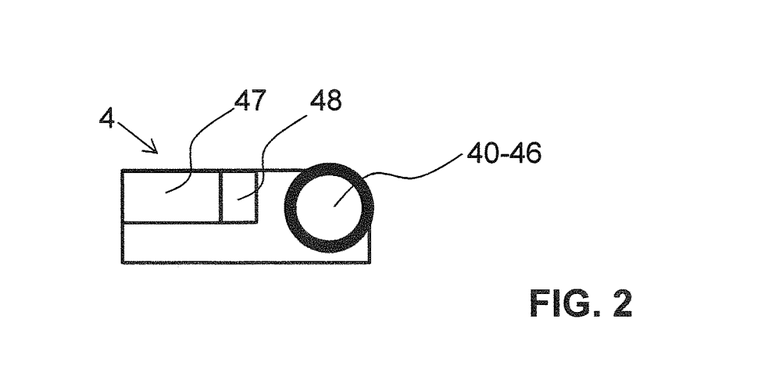
FIG. 2 a schematic detail view of a measuring device with a pressure sensor as used in the VAD of FIG. 1.

In FIG. 2, an exemplary measuring device 4 is shown schematically, which comprises one of the pressure sensors 40-46.

Of course, it would also be possible for the measuring device 4 to have more than a single pressure sensor. If the measuring device 4 comprises more than one pressure sensor, then these sensors can be provided to measure pressure values at approximately the same position in the circulatory system of the patient. For example, a measuring device can comprise several pressure sensors which all measure pressure values inside of the left ventricle 20. Alternatively, one measuring device 4 can have several pressure sensors which measure pressure values at different, remote positions in the circulatory system. For example, one of the pressure sensors can measure the pressure in the right atrium 24 and another pressure sensor which is part of the same measuring device 4 can measure the pressure in the left atrium 22.

The measuring device 4 as shown in FIG. 2 is adapted for wireless communication and comprises a send/receive-unit 47. By means of the send/receive-unit 47, a two-way wireless data communication can be established with the send/receive-unit 14 of the controller 13.

The measuring device 4 shown in FIG. 2 can also comprise a storage module 48. The storage module 48 serves to store an identifier of the measuring device 4, such as for example a specific number that uniquely identifies the measuring device 4 or at least the position of the pressure sensor(s) of the measuring device 4 in the circulatory system of the patient. The identifier can be sent wirelessly from the measuring device 4 to the controller 13. The identification of the measuring device 4 by means of this identifier particularly serves to indicate the position of the measuring device 4 and of its pressure sensor(s) in the circulatory system of the patient.

The identifier is received wirelessly by the controller 13. The controller 13 comprises an integral circuit and a storage module 15 in which for example an assignment table can be stored that assigns a preset control algorithm for regulating the operating point of the blood pump 10 to each of the identifiers of the measuring devices 4. The storage module 48 can also have a first assignment table that assigns a position in the circulatory system of the patient to each of the identifiers and a second assignment table that assigns a control algorithm for regulating the operating point of the blood pump 10 to each of a variety of possible positions.

Preferably, also the control algorithms for regulating the operating point of the blood pump 10 in dependence on the measured pressure values are stored in the storage module 15 of the controller 13.

A first control algorithm can be stored in the storage module 15, according to which a maximum pressure value is identified within a series of pressure values measured over at least one cardiac cycle. The identified maximum pressure value can be used as an estimate for the preload of the heart. The power of the blood pump 10 is then regulated, according to this first control algorithm, linearly dependent on the identified maximum pressure value.

The first control algorithm can particularly be applied, if the corresponding pressure sensor(s) 41, 44, according to the identifier received by the controller 13, are adapted to measure pressure inside of the left ventricle 20 or inside of the right ventricle 23. In this way, the regulation of the operating point of the blood pump 10 is achieved in a particularly robust and reliable way.

A second control algorithm can be stored in the storage module 15, according to which a minimum pressure value is identified within a series of pressure values measured over at least one cardiac cycle. The identified minimum pressure value can be used as an estimate for the preload of the heart. The power of the blood pump 10 is then regulated, according to this second control algorithm, linearly dependent on the identified minimum pressure value.

The second control algorithm can particularly be applied, if the corresponding pressure sensor(s) 43, according to the identifier received by the controller 13, are adapted to measure pressure inside the pulmonary circulation, particularly inside the pulmonary arterial circulation, such as for example inside the pulmonary artery 25. In this way, if the pressure sensor is positioned in the pulmonary circulation, the regulation of the operating point of the blood pump 10 is achieved in a particularly robust and reliable way.

A third control algorithm can be stored in the storage module 15, according to which a temporal mean value is calculated of a series of pressure values measured over at least one cardiac cycle. The power of the blood pump 10 is then regulated, according to this third control algorithm, linearly dependent on the calculated temporal mean value.

The third control algorithm can particularly be applied, if the corresponding pressure sensor(s) 42, 45 or 46, according to the identifier received by the controller 13, are adapted to measure pressure inside the right atrium 24 or inside the left atrium 22 or inside the systemic vein 26 or inside a pulmonary vein. In this way, if the pressure sensor is positioned in the left atrium 22, the right atrium 24, the systemic vein 26 or a pulmonary vein, the regulation of the operating point of the blood pump 10 is achieved in a particularly robust and reliable way.

A fourth control algorithm can be stored in the storage module 15, according to which a pressure value at a specific point in time during the cardiac cycle is identified in a series of pressure values. The specific point in time can for example be end-diastole or the point in time, when one of the cardiac valves opens or closes. The specific point in time can be determined e.g. based on the measured pressure values or based on an ECG measurement. The power of the blood pump 10 is then regulated, according to this fourth control algorithm, linearly dependent on this identified pressure.

The fourth control algorithm can particularly be applied, if the corresponding pressure sensor(s) 41 or 44, according to the identifier received by the controller 13, are adapted to measure pressure inside the right ventricle 23 or inside the left ventricle 20. In this way, a precise estimate for the cardiac preload can be obtained, in order to achieve a particularly physiological regulation of the blood pump 10.

Due to the different control algorithms stored in the controller 13, the biomedical apparatus as shown in FIG. 1 is able to be applied flexibly in accordance to the needs and the limitations indicated by the respective patient. For example, if the pathology of the heart 2 does not allow positioning a pressure sensor inside of the heart 2, then the measuring device 4 can be arranged such that its pressure sensor 43 is positioned inside of the pulmonary artery 25. In comparison to a positioning of the pressure sensor inside of the heart 2, the controller 13 then simply applies a different control algorithm for regulating the power of the blood pump 10, i.e. the second control algorithm instead of the first, the third, or the fourth control algorithm. By applying the appropriate preset control algorithm, robust and reliable regulation of the blood pump 10 can be guaranteed in each case with the same VAD and independently of the positioning of the pressure sensor inside of the circulatory system.

Of course, it is also conceivable to have more than a single measuring device 4 with pressure sensors arranged at different positions in the circulatory system. The controller 13 could then combine the measured pressure values before applying one of the first, second, third or fourth preset control algorithms. It is also possible that a further preset control algorithm is stored in the storage module 15 of the controller 13, according to which further control algorithm the measured pressure values are combined in a certain way, in order to regulate the blood pump 10. Furthermore, it is also possible that the controller 13 is configured to only consider the pressure values measured by one of the pressure sensors or received from one of the measuring devices 4, while discarding the pressure values received from the other pressure sensors, for regulation of the blood pump 10. In such a case, a predefined priority list can be provided in the controller 13 to define which sensor is used for controlling the pump.

Furthermore, the controller 13 can comprise a preset special control algorithm stored in the storage module 15, which special control algorithm is selected by the controller 13 for being applied, if the received signal of the measured pressure values exceeds a certain upper and/or lower limit, or if the desired pump operating point exceeds a certain upper and/or lower limit. In addition or alternatively, it is also possible that an alarm is created in such a case. Further, detection algorithms that run in parallel to the control algorithm, for example by means of ventricular suction detectors, can initiate either alarms or automatic recalibration of the control algorithm, or it can overrule the desired pump operating point. Over- and underpumping can be avoided in this way.

Figure 3:
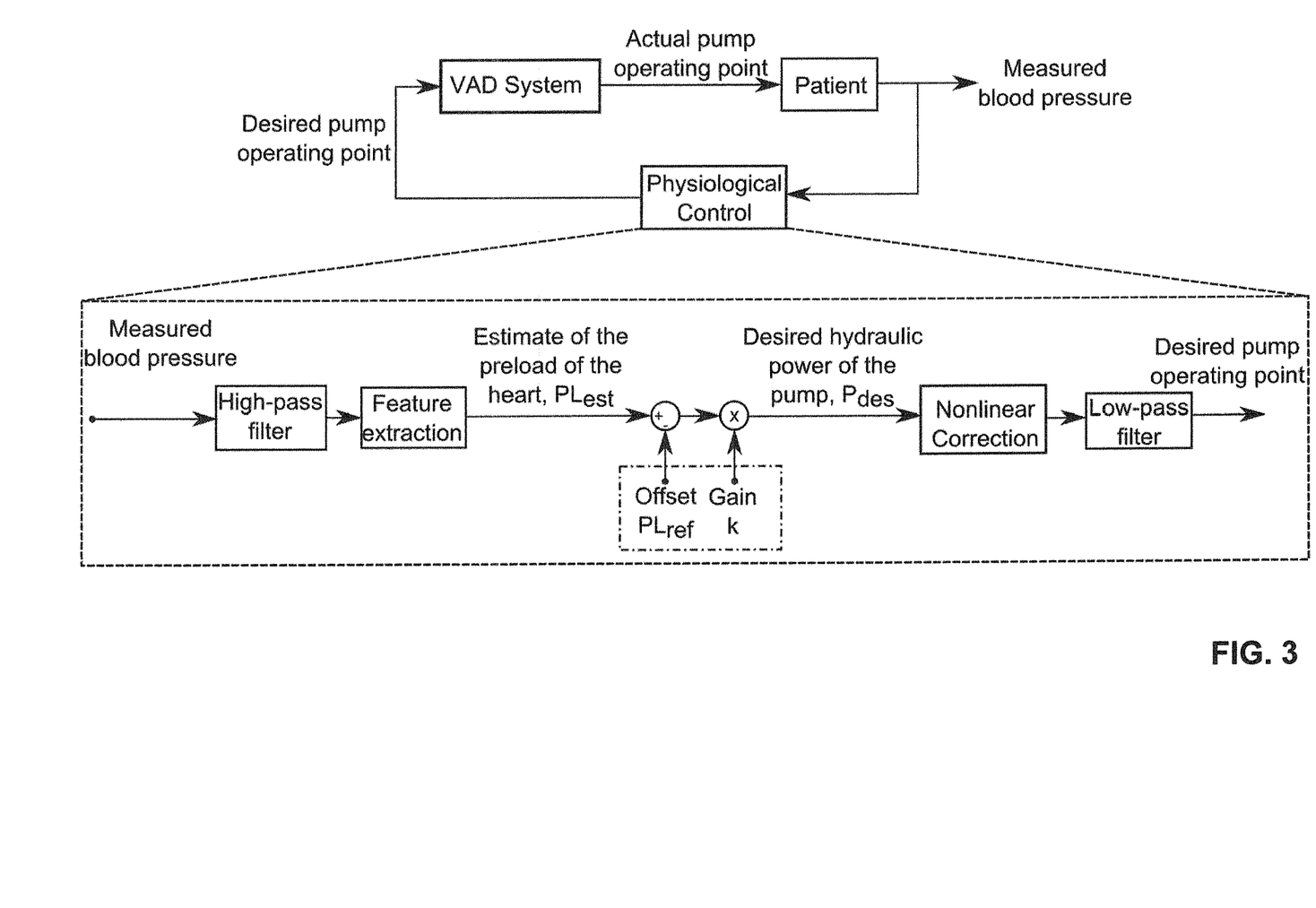
FIG. 3 a schematic representation of the main control structure of a VAD according to the invention.

In FIG. 3, the physiological control structure of the VAD as implemented in the controller 13 is shown. A blood pressure is measured in a blood vessel or in the heart 2 of the patient, and the physiological controller 13 defines a desired pump operating point for the blood pump 10. The resulting power of operation of the blood pump 10 of the VAD system has an effect on the blood that circulates in the circulatory system of the patient and thereby influences the measured blood pressure. Thus, a closed-loop system for regulating the VAD is achieved.

In a first step, as shown in FIG. 3, the signal that reflects the measured blood pressure is subjected to a high-pass filter. The high-pass filter is applied such to the measured signal that long-term drift of the pressure sensor 40-46 is eliminated. The high-pass filter can be a second-order infinite impulse response (IIR) filter, and the cut-off frequency of the filter is chosen such that day/night-cycles are still considered for control, i.e. a cut-off frequency of approximately $1*10$ Hz is applied by the filter.

In a second step, a feature extraction in accordance to one of the different preset control algorithms is carried out. For example, an estimate of the preload of the heart is determined by identifying the maximum or minimum values for a series of pressure values measured over at least one cardiac cycle, e.g. over a time interval of 1.5 to 2.5 seconds, preferably of 2 seconds. Alternatively, a temporal mean value of the pressure values measured over at least one cardiac cycle, e.g. over a time interval of 1.5 to 2.5 seconds, preferably of 2 seconds, can be calculated. A time interval of 1.5 to 2.5 seconds, in particular of 2 s, is preferred to ensure that a reliable input value is detected even for low heart rates. Alternatively, a specific time point in the cardiac cycle can be identified, e.g. the time where end-diastole occurs, and the pressure value at this time point is extracted as an estimate of the preload of the heart. This method is executed on a beat-to-beat basis and thus is repeated for every cardiac cycle.

In the next step, the extracted feature, e.g. the estimate for the left ventricular peak-systolic pressure $PL_{est}$ according to the first control algorithm, forms an input variable which is converted to an output variable by means of a static bijective mapping. Specifically, this mapping can be a linear function in which the output variable is the desired power of the pump $P_{des}$:

$$P_{des}=k(PL_{est}-PL_{ref}),$$

wherein k is the proportional gain (W/mmHg) and $PL_{ref}$ is the offset of the control algorithm obtained during a calibration phase (mmHg).

$PL_{ref}$ of this linear function can be defined as follows: In a calibration phase, a pump operating point $P_{des}$(calibration) is preset by the surgeon independently of the algorithms stored in the controller 13. $PL_{ref}$ is then calculated based on this operating point $P_{des}$(calibration) and based on the measured estimate for the preload of the heart, for example the left ventricular peak-systolic pressure, $PL_{est}$(calibration). The gain k is independent of the calibration and is either predefined or adapted automatically during the application of the respective control algorithm. Predefined default values for the gain k can be stored in the controller and be dependent on the sensor location.

If the extracted feature is an estimate of the preload of the heart based on the second, third or fourth control algorithm, the denotation of the variables and parameters of the above-mentioned linear function need to be adapted accordingly, of course. However, the underlying linear function preferably remains unchanged. In any case, due to this linear function, the controller 13 will always return to the same pump speed, if the same measurement is obtained.

Thus, the controller 13 is a linear controller, which adapts the power of blood pump 10 linearly to the estimate of the preload of the heart. The controller 13 linearly relates an input signal that varies with pre- and afterload variations to the pumping work by controlling the $P_{des}$, and thus imitates the Frank-Starling mechanism.

The output signal $P_{des}$ can then be subjected to a non-linear correction, in order to account for a nonlinear relationship between the desired hydraulic power of the blood pump 10 and the desired pump speed representing the desired operating point of the blood pump 10. The desired pump speed, i.e. the output of the non-linear correction, can in particular be in the form of an output voltage which is used to directly control the blood pump 10. For example, the linear function calculates a desired hydraulic power of the blood pump 10 based on the preload of the heart, and the non-linear correction converts this desired hydraulic power to a desired operating point, e.g. a speed of a rotational blood pump 10 using a predefined nonlinear mapping of these two variables. Such a mapping can be obtained by experimentally identifying the hydraulic characteristics of the blood pump 10. In certain cases, this non-linear correction can be omitted, and the linear law directly calculates the desired operating point of the pump 10, e.g. the desired speed of a rotational pump.

The signal obtained after the non-linear correction can be low-pass filtered, in order to achieve a smooth and steady regulation of the blood pump 10, as shown in FIG. 3. The obtained desired pump operating point, e.g. the speed, is then used to regulate the power of the blood pump 10.

The presented controller 13 according to the embodiment as illustrated FIGS. 1-3 adapts the cardiac output very similar to the physiological circulation, while effectively preventing overpumping and underpumping. The controller 13 shows a high sensitivity towards preload changes and a low sensitivity to afterload changes. The pump speed adaptation with regard to the blood pump 10 is fast and keeps the system in a safe range. The main control structure of the controller 13 is very simple and only two parameters need to be adapted, namely the gain k, and the offset $PL_{ref}$. The adaptation of these parameters, in particular of k, could also be made by the physician, trained medical personnel, or the patient in order to find a comfortable level of perfusion. As long as k is kept between certain limits, the controller 13 retains its safe operation.

Default values for this gain k can be stored in the controller 13 for different sensor locations. Further, methods for automatically adapting this gain k can be included in the controller. Such adaptations can occur based on a predefined look-up table, or by an online estimation of certain hemodynamic parameters.

The invention is of course not limited to the preceding presented embodiment and a plurality of modifications is possible. For example, the controller 13 with the control structure as presented above could also be used for controlling the operating point of a blood pump in an extracorporeal membrane oxygenation (ECMO) apparatus, a heart-lung machine or a dialysis apparatus. The inlet and the outlet cannulas of the VAD do not necessarily be inserted into in the left ventricle 20 and the aorta 3, respectively, but could be inserted at any other location of the circulatory system, depending on the concrete purpose of the biomedical apparatus. A plurality of further modifications is possible.

The invention claimed is:

1. A biomedical apparatus for pumping blood of a human or an animal patient through a secondary intra- or extracorporeal blood circuit, comprising:
    a blood pump for pumping blood,
    an inlet duct connected to the blood pump, for being inserted into a patient's circulatory system, in order to guide blood of the patient to the blood pump,
    an outlet duct connected to the blood pump, for being inserted into the patient's circulatory system, in order to guide blood from the blood pump back to the patient's circulatory system,
    at least two measuring devices each with at least one pressure sensor for measuring pressure values in the patient's circulatory system, and
    a controller for regulating the operating point of the blood pump based on the measured pressure values,
    wherein the controller comprises at least two different preset control algorithms for regulating the operating point of the blood pump based on the measured pressure values, and wherein the controller is configured to select one of these preset control algorithms for being applied in dependence on a position of at least one pressure sensor of the at least two measuring devices in the patient's circulatory system.

2. The biomedical apparatus of claim 1, wherein at least one of the at least two different preset control algorithms causes the controller to determine an estimate for the preload of the heart based on an identification of a minimum of the measured pressure values, in order to regulate the operating point of the blood pump based on this determined estimate for the preload of the heart.

3. The biomedical apparatus of claim 1, wherein at least one of the at least two different preset control algorithms causes the controller to calculate a temporal mean value of the measured pressure values over at least one cardiac cycle, in order to regulate the operating point of the blood pump based on this calculated temporal mean value.

4. The biomedical apparatus of claim 1, wherein at least one of the at least two different preset control algorithms causes the controller to identify a pressure at a specific point in time during the cardiac cycle based on the measured pressure values, in order to regulate the operating point of the blood pump based on this identified pressure.

5. The biomedical apparatus as claimed in claim 1, wherein the at least one pressure sensor is configured to measure the pressure values inside of the left ventricle or the right ventricle of the heart of the patient, and wherein according to at least one preset control algorithm an estimate for a preload of the heart is determined based on an identification of a maximum of the pressure values measured by this pressure sensor inside of the left ventricle or the right ventricle, in order to regulate the operating point of the blood pump based on this determined estimate for the preload of the heart.

6. The biomedical apparatus as claimed in claim 1, wherein the at least one pressure sensor is configured to measure the pressure values inside of the pulmonary arterial circulation of the patient, and wherein according to at least one preset control algorithm an estimate for the preload of the heart is determined based on an identification of a minimum of the pressure values measured by this pressure sensor inside of the pulmonary arterial circulation, in order to regulate the operating point of the blood pump based on this determined estimate for the preload of the heart.

7. The biomedical apparatus as claimed in claim 1, wherein the at least one pressure sensor is configured to measure the pressure values inside of the left atrium or the right atrium of the heart or inside of the pulmonary or systemic vein of the patient, and wherein according to at least one preset control algorithm a temporal mean value is calculated of the pressure values measured by this pressure sensor inside of the left atrium or the right atrium or inside of the pulmonary or systemic vein over at least one cardiac cycle, in order to regulate the operating point of the blood pump based on this calculated temporal mean value.

8. The biomedical apparatus as claimed in claim 1, wherein the at least one pressure sensor is configured to measure the pressure values inside of the left ventricle or the right ventricle of the heart of the patient, and wherein according to at least one preset control algorithm a pressure at a specific point in time during the cardiac cycle is identified based on the pressure values measured by this pressure sensor inside of the left ventricle or the right ventricle, in order to regulate the operating point of the blood pump based on this identified pressure.

9. The biomedical apparatus as claimed in claim 1, wherein the at least two different preset control algorithms of the controller are at least two of the following four control algorithms:
    a first control algorithm, according to which an estimate for the preload of the heart is determined based on an identification of a maximum of the measured pressure values, in order to regulate the operating point of the blood pump based on this determined estimate for the preload of the heart,
    a second control algorithm, according to which an estimate for the preload of the heart is determined based on an identification of a minimum of the measured pressure values, in order to regulate the operating point of the blood pump based on this determined estimate for the preload of the heart,
    a third control algorithm, according to which a temporal mean value is calculated of the measured pressure values over at least one cardiac cycle, in order to regulate the operating point of the blood pump based on this calculated temporal mean value, and
    a fourth control algorithm, according to which a pressure at a specific point in time during the cardiac cycle is identified based on the measured pressure values, in order to regulate the operating point of the blood pump based on this identified pressure.

10. The biomedical apparatus as claimed in claim 9, wherein the controller is configured to regulate the operating point of the blood pump, such that a linear relationship is established between the estimate for the preload of the heart or the temporal mean value or the pressure at a specific point in time during the cardiac cycle on the one hand and the power of the blood pump on the other hand.

11. The biomedical apparatus as claimed in claim 9, wherein the biomedical apparatus is a Mechanical Circulatory Support (MCS) device.

12. The biomedical apparatus as claimed in claim 1, wherein the at least two measuring devices comprises a send-unit and the controller comprises a receive-unit, for wirelessly transmitting a signal that reflects the measured pressure values from the at least one measuring device to the controller.

13. The biomedical apparatus as claimed in claim 1, wherein the at least two measuring devices is adapted to transmit an identifier to the controller, the identifier reflecting the position of the at least one pressure sensor in the patient's circulatory system.

14. The biomedical apparatus as claimed in claim 13, wherein the controller is configured to select one of the preset control algorithms for being applied in dependence on the identifier transmitted by the at least two measuring devices.

15. The biomedical apparatus as claimed in claim 1, further comprising a high-pass filter for filtering a signal that reflects the measured pressure values, wherein the high-pass filter is designed such that a possible long-term drift of the at least one pressure sensor is eliminated from the signal, but that day/night cycles are still reflected in the signal.

16. The biomedical apparatus as claimed in claim 1, wherein the controller is adapted to superimpose the regulation of the operating point of the blood pump with a periodic signal being synchronized to the cardiac cycle.

17. A method for operating a biomedical apparatus for pumping blood of a human or an animal patient through a secondary intra- or extracorporeal blood circuit, wherein the biomedical apparatus comprises a blood pump for pumping blood, an inlet duct connected to the blood pump, for being inserted into a patient's circulatory system, in order to guide blood of the patient to the blood pump, an outlet duct connected to the blood pump, for being inserted into the patient's circulatory system, in order to guide blood from the blood pump back to the patient's circulatory system, and at least two measuring devices each with at least one pressure sensor, the method comprising:

measuring pressure values in the patient's circulatory system with at least one pressure sensor of the two measuring devices, and regulating an operating point of the blood pump based on the measured pressure values, wherein regulating the operating point of the blood pump comprises determining a position of the at least one pressure sensor in the patient's circulatory system, and selecting and applying one of at least two different preset control algorithms for regulating the operating point of the blood pump based on the measured pressure values based on the determined position of the at least one pressure sensor in the patient's circulatory system.

18. The biomedical apparatus of claim 1, wherein at least one of the at least two different preset control algorithms causes the controller to determine an estimate for the preload of the heart based on an identification of a maximum of the measured pressure values, in order to regulate the operation point of the blood pump based on this determined estimate for the preload of the heart.

19. The biomedical apparatus as claimed in claim 11, wherein the biomedical apparatus is a Ventricular Assist Device (VAD).

20. The biomedical apparatus as claimed in claim 1, wherein the controller is adapted to be manually configured by medical personnel to apply one of the preset control algorithms.

21. The biomedical apparatus as claimed in claim 14, wherein the controller comprises a storage module in which an assignment table is stored, which assigns one of the preset control algorithms to the identifier.

\* \* \* \* \*